United States Patent
Nollert

(10) Patent No.: US 11,602,389 B2
(45) Date of Patent: Mar. 14, 2023

(54) CATHETER SYSTEM FOR CRYOABLATION OF THE VAGUS NERVE

(71) Applicant: Georg Daniel Andreas Nollert, Strasslach (DE)

(72) Inventor: Georg Daniel Andreas Nollert, Strasslach (DE)

(*) Notice: Subject to any disclaimer, the term of this patent is extended or adjusted under 35 U.S.C. 154(b) by 362 days.

(21) Appl. No.: 16/905,367

(22) Filed: Jun. 18, 2020

(65) Prior Publication Data
US 2021/0000520 A1 Jan. 7, 2021

(30) Foreign Application Priority Data
Jul. 2, 2019 (DE) .................. 10 2019 117 871.1

(51) Int. Cl.
| A61B 18/02 | (2006.01) |
| A61B 18/00 | (2006.01) |
| A61B 90/00 | (2016.01) |

(52) U.S. Cl.
CPC .............. *A61B 18/02* (2013.01); *A61B 90/39* (2016.02); *A61B 2018/0022* (2013.01); *A61B 2018/00047* (2013.01); *A61B 2018/00494* (2013.01); *A61B 2018/00755* (2013.01); *A61B 2018/0212* (2013.01); *A61B 2018/0262* (2013.01); *A61B 2090/3966* (2016.02)

(58) Field of Classification Search
CPC ............ A61B 18/02; A61B 2018/0212; A61B 2018/0262; A61B 2018/00005–00035; A61B 2018/00047; A61B 2018/00494; A61B 2018/00875
See application file for complete search history.

(56) References Cited

U.S. PATENT DOCUMENTS

| 6,427,089 | B1 | 7/2002 | Knowlton | |
| 2010/0100087 | A1* | 4/2010 | Mazzone | A61B 18/02 29/428 |
| 2015/0126986 | A1* | 5/2015 | Kelly | A61B 18/02 606/23 |
| 2016/0038212 | A1 | 2/2016 | Ryba et al. | |
| 2018/0116704 | A1 | 5/2018 | Ryba et al. | |
| 2019/0262056 | A1* | 8/2019 | Yang | A61B 18/02 |
| 2020/0069366 | A1* | 3/2020 | Clark | A61B 18/1492 |
| 2021/0077173 | A1* | 3/2021 | Diao | A61B 18/02 |
| 2021/0251677 | A1* | 8/2021 | Burnett | A61F 7/007 |

OTHER PUBLICATIONS

First Examination Report issued by German Patent Office for German Patent Application No. 102019117871.1 dated May 22, 2020.

* cited by examiner

*Primary Examiner* — Thaddeus B Cox
(74) *Attorney, Agent, or Firm* — Thomas | Horstemeyer, LLP

(57) ABSTRACT

A catheter system for cryoablation of the stomach, comprising: a catheter and at least one inflatable cryoballoon which is fastened to the catheter and exhibits a contact curve along which the cryoballoon can be brought into contact with the fundus, wherein the contact curve is a closed curve on the surface of the cryoballoon, and the cryoballoon contains a first cooling arrangement which extends along less than three quarters of the length of the contact curve.

9 Claims, 6 Drawing Sheets

CATHETER SYSTEM FOR CRYOABLATION OF THE VAGUS NERVE

CROSS-REFERENCE TO RELATED APPLICATION

This application claims the benefit of and priority to German Patent Application No. 10 2019 117 871.1, filed Jul. 2, 2019, the contents of which being incorporated by reference in their entirety herein.

FIELD OF THE INVENTION

The present invention relates to a catheter system for cryoablation of the stomach, in particular for reducing gastric motility in the case of obesity.

BACKGROUND

Obesity is the cause of many lifestyle diseases such as diabetes, damage to joints, or heart failure. In addition to non-invasive treatments such as dieting or sporting activities, there is also the countermeasure of invasive treatments such as a sleeve gastrectomy, gastric band operation, intragastric balloon, gastric bypass, gastric pacemaker or injecting Botox.

It has been shown that obesity can also be treated by cryoablation of the vagus nerve (nervus vagus). The vagus nerve has an anterior trunk (truncus vagus anterior) and a posterior trunk (truncus vagus posterior), wherein the nerve is completely or partially (for example only the anterior or posterior trunk) frozen, such that gastric motility is reduced and the effect of "hunger hormones" such as ghrelin and insulin is reduced.

It has been possible to show in animals that vagal activity contributes to weight increase and that ablation of the vagus nerve can partially correct metabolic syndrome and in particular hyperinsulinemia. The vagus nerve is currently either severed in an operation or functionally restricted by other methods. The vagotomy method seems very promising, since it reduces the patient's hunger. There is a human study in which the posterior trunk of the vagus nerve was frozen past the transition from the oesophagus to the stomach by cryoablation guided in a computer tomograph, wherein a cryoprobe is guided from the back to the posterior trunk using a needle. Alternatively, the vagus nerve was blocked in a laparoscopic operation. One problem with these methods is that only a few interventional radiologists can perform this method in CT or an operation becomes necessary.

BRIEF SUMMARY OF INVENTION

The inventor is now pursuing the approach of ablating the vagus nerve by means of a catheter system, transmurally out of the stomach through the gastric wall, in particular in the region of the gastric fundus.

The catheter system comprises a catheter and at least one inflatable cryoballoon. The cryoballoon is fastened to the catheter and exhibits a contact curve along which the cryoballoon can be brought into contact with the fundus. The contact curve is a closed curve on the surface of the cryoballoon. The cryoballoon contains a first cooling arrangement which extends along less than three quarters of the length of the contact curve.

A catheter is usually an elongated flexible tube. The catheter extends along its longitudinal axis. The circumference of the catheter extends in a plane which is perpendicular to the longitudinal axis of the catheter, wherein the circumference denotes the line formed in this plane by the outermost points on the surface of the catheter.

A catheter has a distal end and a proximal end, wherein the distal end is intended to be inserted into a body through an opening. The at least one cryoballoon is for example arranged at the distal region of the catheter, such that it can be introduced into the body together with the distal end of the catheter, wherein the distal region comprises for example the last 2, 5 or 10 centimetres of the catheter at its distal end. The cryoballoon can also be arranged directly at the distal end of the catheter. The distal end of the catheter can comprise an extension, for example in the form of a PVC, silicone or Wiruthan tube which simplifies inserting the catheter.

In the case of a catheter system for gastric cryoablation, the distal end of the catheter—together with the at least one cryoballoon—is for example inserted into the stomach through the oesophagus. In the following, the term "inserting the catheter" denotes inserting the distal end of the catheter.

A cryoballoon is a balloon which can be cooled on at least a part of its surface, in order to perform cryoablation. This part extends along the contact curve which forms a line along which the cryoballoon is in contact with the gastric wall while it is being used. The contact curve can lie in a two-dimensional plane, and in a special case can be a circle, or can be a three-dimensional curve, wherein the contact is usually not just linear but rather extends on one or both sides of the contact curve, i.e. it is an elongated contact area.

Since the first cooling arrangement extends along less than three quarters of the length of the contact curve, this means that less than three quarters of the circumference of the cryoballoon is cooled by the first cooling arrangement. This enables a targeted ablation of a part of the vagus nerve.

The at least one cryoballoon is deflated while the catheter is being inserted. In order for a cryoballoon to assume its desired shape and for example abut the inner side of the gastric wall, the interior of the cryoballoon is filled with a suitable filler, for example air or a filling liquid such as for example a saline solution, through a filling conduit. Filling the cryoballoon in particular causes the cryoballoon to abut the gastric wall along the contact curve. Depending on the fill level of the cryoballoon, the latter abuts the gastric wall not just linearly but rather over a contact area through which the contact curve extends.

The cryoballoon is for example inflated in the stomach, and the catheter together with the cryoballoon is retracted in the proximal direction, such that the cryoballoon abuts the gastric wall along the contact curve. The catheter together with the cryoballoon is for example advanced into the stomach in the working channel of a gastroscope.

In one embodiment of the invention, the catheter system comprises a reservoir for the filler, the reservoir being connected to the filling conduit at the proximal end of the catheter. The catheter system optionally comprises a conveying device by means of which the filler can be conveyed from the reservoir into the interior of the cryoballoon and/or from the interior into the reservoir.

In one embodiment, the catheter system comprises a pressure sensor which measures the pressure in the filling conduit as the interior of the cryoballoon is filled. It is thus possible to output an indication and/or stop the conveying device as soon as a predetermined threshold value of the pressure in the filling conduit is reached or exceeded. Alternatively or additionally, the catheter system can comprise a pressure limiter which automatically limits the pressure in the filling conduit. It is thus possible to prevent overfilling of the cryoballoon.

In one embodiment, the cryoballoon comprises two measuring electrodes which are arranged on its surface on different sides of the contact curve. This means that the contact curve extends between the measuring electrodes. The measuring electrodes extend along the contact curve, wherein the length of the measuring electrodes is greater than their width, for example by a factor of 2, 5, 10 or more.

The catheter system also for example comprises evaluation electronics designed to measure the impedance between the two measuring electrodes. To this end, the evaluation electronics are electrically connected to the two measuring electrodes, for example by means of conduits which extend through the catheter, or wirelessly. The evaluation electronics can also be arranged within the cryoballoon, and the result of the impedance measurement can be transmitted to a receiver, for example by a wire connection via a conduit within the catheter, or wirelessly. The measurement value, for example the current which flows between the two measuring electrodes when a particular voltage is applied, is transmitted to the evaluation electronics, which calculate the impedance.

The impedance, which in a special case is a resistance which can be equivalently expressed by its conductivity, correlates with the degree of ablation of the tissue and therefore vagus nerve. If the measured impedance exceeds a defined limit value, this is optionally interpreted to mean that transmural ablation is complete. In this case, ablation can be automatically terminated.

It should be noted that the measuring electrodes and optionally also the evaluation electronics are not limited to a catheter system in accordance with the invention, in which the first cooling arrangement extends over less than three quarters of the length of the contact curve, but rather can also in particular be used in a catheter system for circumferential ablation, in which ablation is performed along the entire contact curve. This document also relates to a catheter system comprising two measuring electrodes and an optional evaluation unit, in which the first cooling arrangement extends along the entire length of the contact curve.

In one embodiment of the invention, the cryoballoon exhibits the shape of at least a part of the fundus. This is an asymmetrical shape which for example corresponds to the average shape of at least a part of the fundus, such as can for example be ascertained by studies. One advantage of this shape is that the cryoballoon automatically aligns within the fundus as it is inflated, for example around the longitudinal axis of the catheter, and thus assumes a known orientation relative to the stomach.

Alternatively, the cryoballoon can exhibit a generic shape, for example a rotationally symmetrical (for example, spherical or toroidal) shape or a mirror-symmetrical shape. Such a cryoballoon adapts to the shape of the fundus as it is inflated due to its elasticity.

In one embodiment of the invention, the proximal end of the cryoballoon comprises a region in which the contact curve extends and the cross-sectional area of the cryoballoon increases continuously from the proximal to the distal. The region in which the contact curve extends comprises for example 10, 20, 25, 40 or 50 percent of the proximodistal extent of the cryoballoon. The increasing size of the cryoballoon in this region means that when the catheter is retracted in the proximal direction, the cryoballoon abuts the gastric wall via a region which is cooled by the first cooling arrangement.

In one embodiment, the first cooling arrangement extends over at most half the length of the contact curve, for example 40% or less of the length or 40% to 49% of the length of the contact curve. Thus, at most half of the contact area between the cryoballoon and the gastric wall is cooled, thus enabling the gastric wall to be selectively cooled. The trunks of the vagus nerve can thus for example be ablated separately and in a targeted way.

In one embodiment of the invention, the first cooling arrangement comprises at least one Peltier element. If a current is passed through the Peltier element, it generates a temperature difference which can be used for the purpose of ablation.

In one embodiment of the invention, the cooling arrangement is a cooling conduit for a cooling medium such as for example a cooling liquid, and the catheter contains at least one conveying conduit which is connected to the cooling conduit. The cooling medium is a cooled medium which flows through the cooling conduit and thus cools the surface of the cryoballoon in the region of the cooling arrangement.

The cooling medium is conveyed into the cooling conduit via the conveying conduit. If there is a single conveying conduit, it serves to feed the cooling medium to the cooling conduit and drain the cooling medium from the cooling conduit in chronological succession. If there are two conveying conduits which are connected to different ends of the cooling conduit, a circulation of the cooling medium through the catheter and the cooling conduit is possible, thus enabling continuous ablation to be achieved.

In one embodiment of the invention, the catheter system comprises a reservoir for the cooling medium. This reservoir is connected to the at least one conveying conduit at the proximal end of the catheter. The catheter system optionally also comprises a conveying device which conveys the cooling medium from the reservoir into the cooling conduit via the conveying conduit.

In one embodiment of the invention, the catheter system also comprises a cooling device designed to cool a cooling medium before it is conveyed into the cooling conduit. The cooling device can for example cool the cooling medium in the reservoir or in a conduit from the reservoir into the cooling conduit.

In one embodiment of the invention, the catheter comprises a depth scale by means of which the insertion depth of the catheter into a body can be ascertained. If the anatomy is known, the insertion depth of the catheter corresponds to the position or positions of the at least one cryoballoon in for example the stomach. In the present case, the insertion depth denotes the length of the portion of the catheter which is inserted into the body. Another option is to ascertain, for example by means of another catheter, the length of the trajectory between the entry point into the body and a point in the stomach such as the pylorus or the transition into the duodenum, in order to thence determine the required insertion depth of the catheter in accordance with the invention.

In one embodiment of the invention, the cryoballoon contains a second cooling arrangement which extends along the contact curve in a region which is not occupied by the first cooling arrangement. The first and second cooling arrangements thus cover different regions along the contact curve. By appropriately controlling the cooling arrangements, it is then possible to perform ablation differently at different locations, for example due to different cooling durations or temperatures. The second cooling arrangement can exhibit any of the aforesaid structures. If any of two or more cooling arrangements are a cooling conduit, then in one embodiment of the invention, each of the cooling conduits is connected to at least one conveying conduit, such that the cooling medium can flow through the cooling conduits in a separately controllable way. The conveying conduits can be supplied from a shared reservoir or from multiple separate reservoirs.

In accordance with the invention, the cryoballoon can also contain more than one second cooling arrangement, wherein the cooling arrangements preferably do not overlap along the contact curve. It is however possible for the cooling arrangements to directly adjoin each other.

In one embodiment, the first and second cooling arrangements extend together over the entire length of the contact curve. This also enables circumferential ablation. In this embodiment, it is likewise possible for the two cooling arrangements to be cooling conduits supplied by a shared conveying conduit.

In one embodiment of the invention, the cryoballoon comprises at least one radiopaque marker, for example at least 3, 4, 5 or more radiopaque markers. A radiopaque marker attenuates X-ray radiation in such a way that the marker can be clearly identified in an X-ray image or CT recording. If the radiopaque markers are identified in corresponding recordings, and their respective position is ascertained, it is possible to thence ascertain the size of the inflated cryoballoon and/or the position of the cryoballoon, for example relative to the fundus. It is thus for example possible to verify, before actual ablation is performed, whether the contact curve of the cryoballoon is abutting the desired point in the gastric wall.

In one embodiment of the invention, the cryoballoon comprises at least one optical marker, for example at least 2, 3, 4, 5 or more optical markers. An optical marker can be identified in an endoscopy, thus enabling the ablation area to be localised, for example relative to anatomical landmarks.

The catheter optionally comprises one or more markers from which the orientation of the catheter and therefore cryoballoon can be determined.

It is within the scope of the disclosure in this document to combine one or more embodiments with each other, wherever technically possible.

BRIEF DESCRIPTION OF THE DRAWINGS

The present invention shall be described in more detail on the basis of specific example embodiments. The corresponding figures, which are not to scale, show.

DETAILED DESCRIPTION

Figure 1:
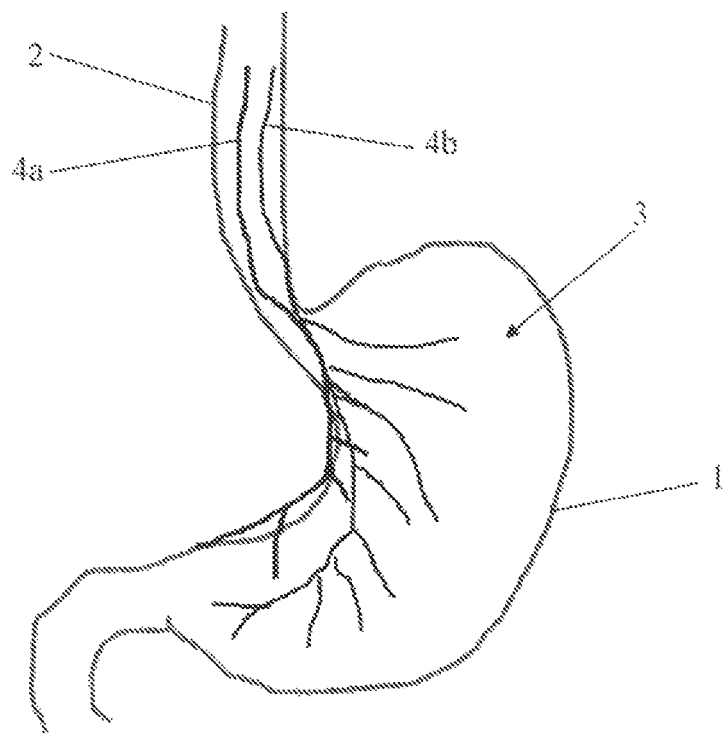
FIG. 1 is a schematic view of a stomach and the vagus nerve.

FIG. 1 shows a schematic view of a stomach 1. The upper region of the stomach 1, into which the oesophagus 2 emerges, is referred to as the fundus 3. FIG. 1 also schematically shows the anterior vagal trunk (truncus vagus anterior) 4a and the posterior vagal trunk (truncus vagus posterior) 4b which together form a part of the vagus nerve (Nervus vagus) 4. The two trunks 4a and 4b of the nerve extend in the body in front of and behind the stomach 1, respectively.

Figure 2:
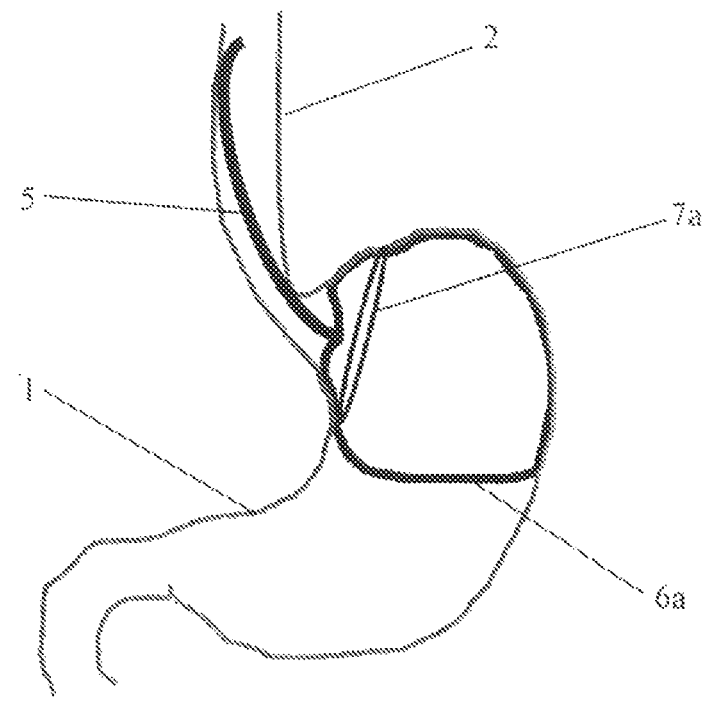
FIG. 2 is the schematic view of FIG. 1, featuring a catheter system comprising a cryoballoon in accordance with a first embodiment.

FIG. 2 shows the schematic view of the stomach 1 from FIG. 1, featuring a catheter system in accordance with a first embodiment. The catheter system consists of a catheter 5, the distal end of which can be inserted up to and into the fundus 3 via the oesophagus 2, wherein the proximal end of the catheter 5 (not shown) remains outside the body.

A cryoballoon 6 is arranged at the distal end of the catheter 5. It is inflatable and is introduced, while deflated, into the fundus 3 together with the distal end of the catheter 5. The cryoballoon 6 and the distal end of the catheter 5 can for example be introduced into the fundus 3 directly or through the working channel. The cryoballoon 6 can be arranged at the distal end of the catheter 5 or at a distance of up to 5 or 10 cm.

FIG. 2 shows a cryoballoon 6a, as part of the catheter system, exhibiting the shape of the fundus 3.

A filling conduit (not shown in the figures) extends within the catheter 5 and is connected to the interior of the cryoballoon 6. A filling medium such as air or a liquid, for example a saline solution, can be introduced into the cryoballoon 6a from outside the body via the filling conduit, such that the cryoballoon 6 is inflated.

Due to its shape, the cryoballoon 6a automatically aligns in a predetermined position within the fundus 3. This results in a contact line 7a between the balloon 6a and the wall of the stomach 1. The contact curve 7a is a closed curve.

Figure 3:
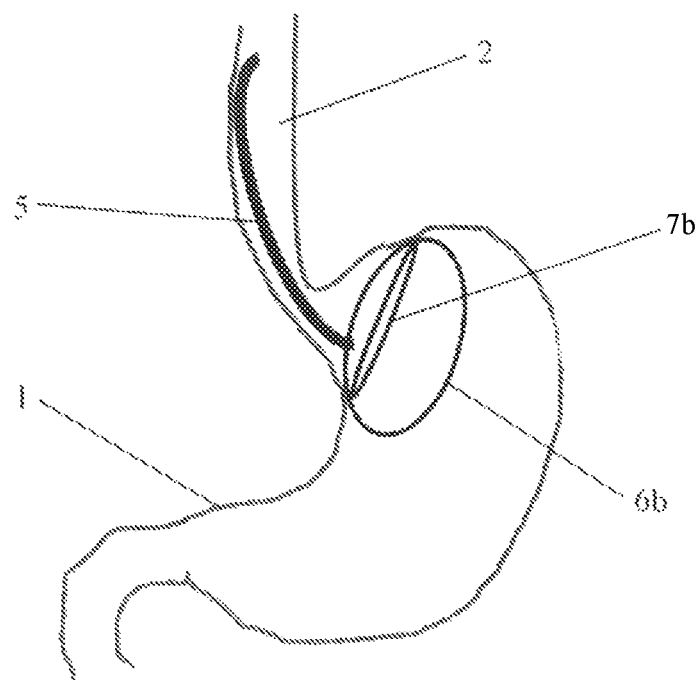
FIG. 3 is the schematic view of FIG. 1, featuring a catheter system comprising a cryoballoon in accordance with a second embodiment.

FIG. 3 shows the schematic view of FIG. 1, featuring a catheter system comprising a cryoballoon 6b of a second embodiment. The cryoballoon 6b does not exhibit a shape adapted to the fundus 3 but rather a generic shape such as for example a spherical shape or a rotationally symmetrical shape having an oval or elliptical cross-section. The cryoballoon 6b abuts the wall of the stomach 1 along the contact curve 7b.

It should be noted that a cryoballoon 6 usually abuts the wall of the stomach 1 not just linearly along the contact curve 7 but rather over an area in a region of the surface of the cryoballoon 6 in which the contact curve 7 extends. In this document, the reference sign 6 describes a cryoballoon shaped in any way, and the reference sign 7 describes a contact curve shaped in any way, while additional letters relate to a particular embodiment.

If the contact curve 7 is circular, it has a diameter of for example 5 to 7 cm. When inflated, the cryoballoon 6 has a volume of for example 400 to 500 ml. A typical diameter of a spherical cryoballoon or a rotationally symmetrical cryoballoon having an oval or elliptical cross-sectional area is for example 10 cm.

Figure 4:
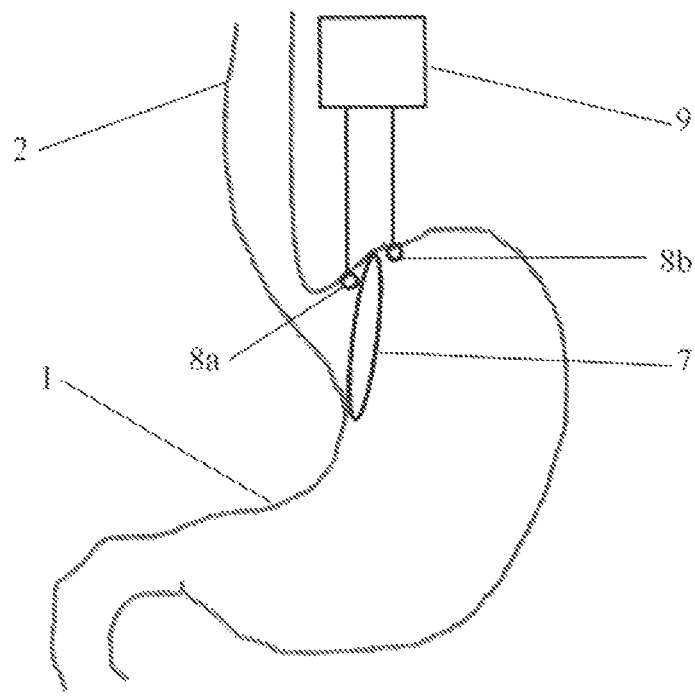
FIG. 4 is a schematic view of the stomach, featuring a contact curve, two measuring electrodes and evaluation electronics.

FIG. 4 shows a schematic view of the stomach 1, featuring a contact curve 7, two measuring electrodes 8a and 8b and evaluation electronics 9. By means of the measuring electrodes 8, the evaluation electronics 9 ascertain the impedance of the tissue between the electrodes 8a and 8b.

Figure 5:
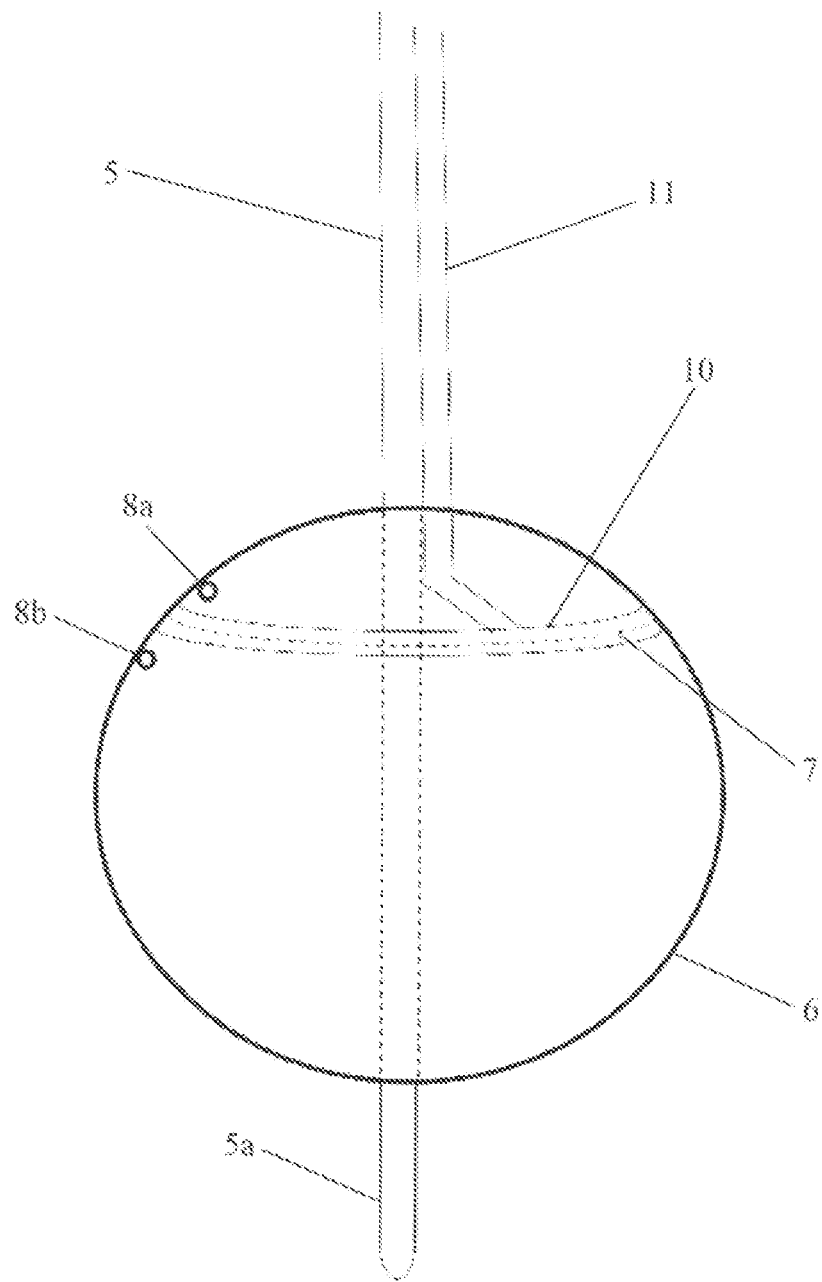
FIG. 5 is a schematic view of the structure of a cryoballoon.

FIG. 5 shows a schematic view of an example structure of a cryoballoon 6. A first cooling arrangement 10, which in the present example is a cooling conduit, extends along the contact curve 7. It can however also be any other type of cooling arrangement, for example one or more Peltier elements.

The cooling arrangement 10 is arranged on or directly below the surface of the cryoballoon 6 and extends over less than three quarters of the length of the contact curve 7. This means that the cooling arrangement does not cool the entire circumference of the contact region between the cryoballoon 6 and the wall of the stomach 1 but rather only a part of the circumference, such that for example each of the trunks 4a and 4b of the vagus nerve 4 can be cooled separately.

By means of a conveying conduit 11, a cooling medium flows through the cooling conduit 10. The conveying conduit 11 extends within the catheter 5 or along the outer sleeve of the catheter 5 and is for example connected to a reservoir (not shown) for the cooling liquid. A second conveying conduit is optionally provided via which the cooling liquid is conveyed out of the cryoballoon 6, such that this results in a closed circulation for the cooling liquid.

FIG. 5 shows the location of the two measuring electrodes 8a and 8b. They lie on the surface of the cryoballoon 6, on different sides on the contact curve 7. One of the measuring electrodes lies inside the contact curve 7, and one outside. The two measuring electrodes 8a and 8b preferably lie opposite each other with respect to the contact curve 7, for example on a straight line perpendicular to the contact curve 7. The distance between the two electrodes 8a and 8b and the contact curve 7 is for example identical.

In the representation of FIG. 5, the cryoballoon 6 is not arranged at the distal end of the catheter 5 but rather at a distance from it. A part 5a of the catheter 5 thus protrudes beyond the inflated cryoballoon 6. This simplifies inserting the catheter 5.

In one embodiment in which the cryoballoon 6 is not arranged at the distal end of the catheter 5 but rather at a distance from it, the cryoballoon 6 preferably surrounds the entire circumference of the catheter 5, such that the cryoballoon 6 can form a closed contact curve 7 with the wall of the stomach 1.

Figure 6:
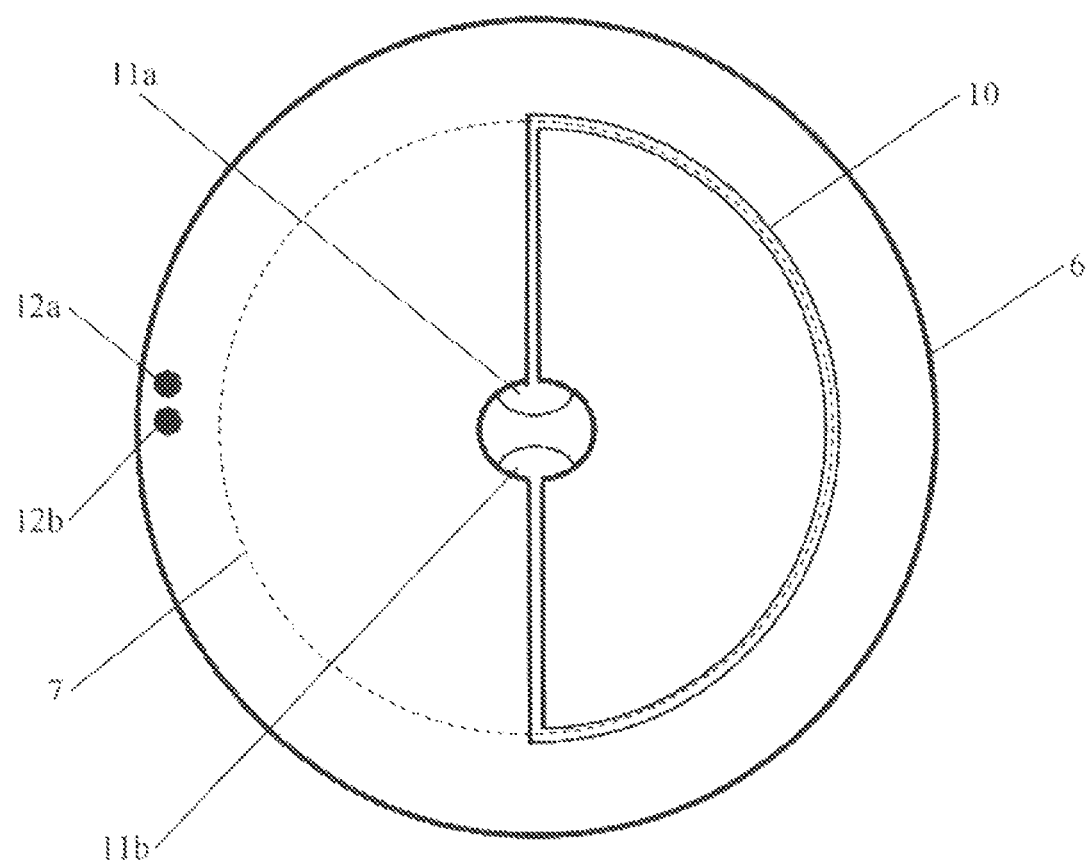
FIG. 6 is a second schematic view of the structure of the cryoballoon.

Contrary to FIG. 5, FIG. 6 shows a schematic plan view onto the cryoballoon 6. As can be seen from FIG. 6, the cooling arrangement 10 extends along less than three quarters of the length of the contact curve 7. In the present example, the first cooling arrangement 10 extends along half the contact curve.

The conveying conduits 11a and 11b are also shown, wherein each of the conveying conduits 11 is connected to a different end of the cooling conduit 10. The cooling liquid is conveyed through the conveying conduit 11a into the cooling conduit 10 and out of the cooling conduit 10 via the conveying conduit 11b. The continuous flow of the cooling medium through the cooling conduit 10 enables continuous ablation of the vagus nerve.

FIG. 6 also shows that the cryoballoon 6 bears optional markers 12a and 12b on its surface. The markers 12 are radiopaque and thus identifiable in medical images based on X-ray radiation such as X-ray images or CT images. The position and/or alignment of the cryoballoon 6, and therefore the first cooling arrangement 10, within the stomach 1 can be detected on the basis of the markers 12. The cryoballoon 6 can in particular be navigated to a desired position. The size of the cryoballoon 6 can also be calculated from the distances between the markers 12. It is then for example possible to stop inflating the cryoballoon 6 as soon as the distance between two defined markers 12 reaches a defined limit value.

FIG. 6 shows two markers 12; the cryoballoon 6 can however also contain fewer or more markers, for example 3, 4, 5 or 6 markers.

Figure 7:
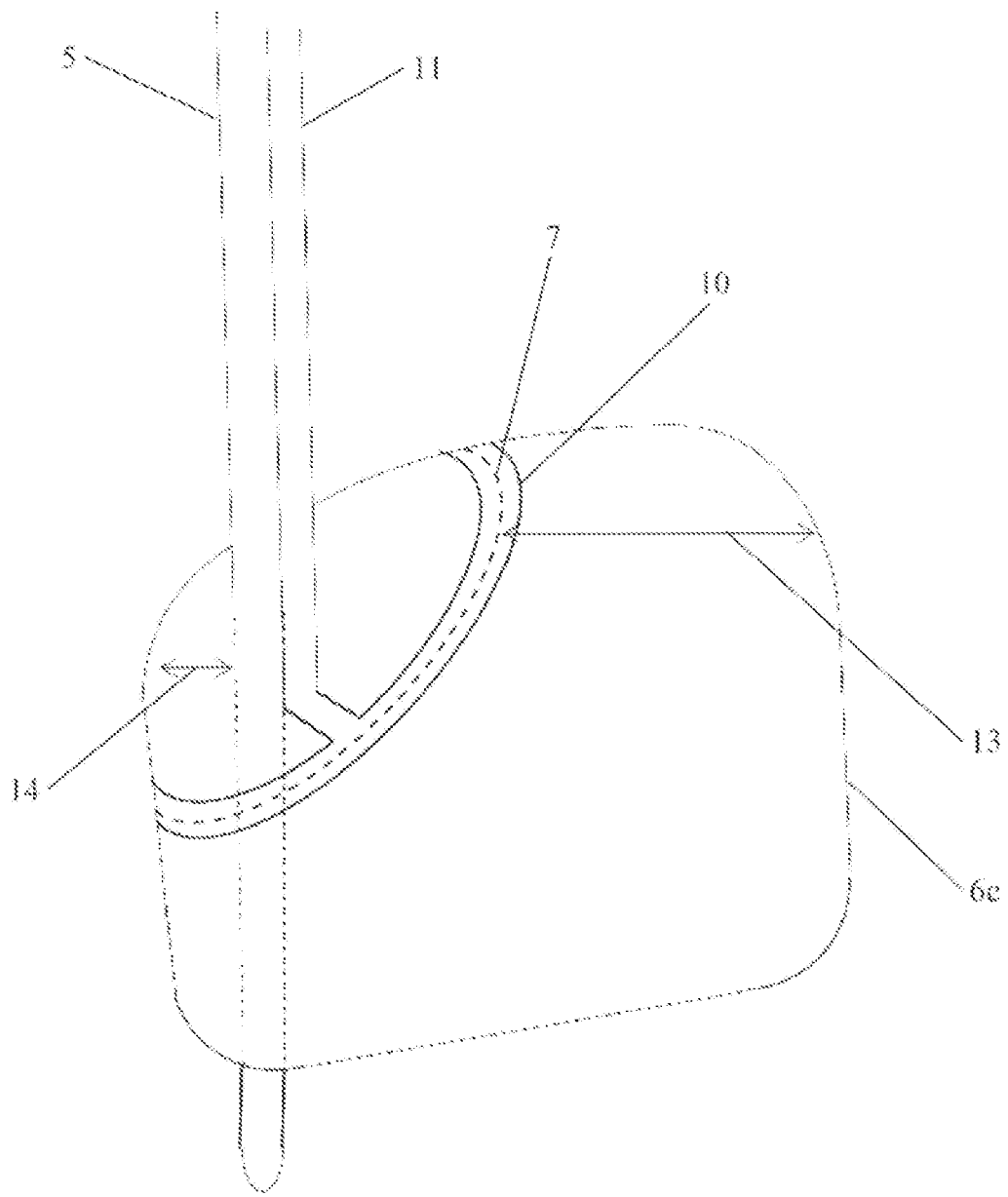
FIG. 7 is a schematic view of a third embodiment of a cryoballoon.

FIG. 7 shows a schematic view of a third embodiment of the cryoballoon, in the form of the cryoballoon 6c. The cryoballoon 6c has a basically cuboidal shape in which one of the shortest edges has been removed by a section comprising a plane. The contact curve 7 lies on the sectional area, and the first cooling element 10 lies directly below that.

The distance 13 between the first cooling arrangement 10 and the smallest non-sectioned rectangle of the cuboid is for example 3 to 5 cm, in particular 4 cm. The distance 14 between the catheter 5 and the smallest sectioned rectangle of the cuboid is for example 0.5 to 1.5 cm, in particular 1 cm.

This shape of the cryoballoon 6c, which is connected eccentrically to the catheter 5, approximately replicates the shape of the fundus 3, but is easier to manufacture than a cryoballoon which exactly replicates the shape of the fundus 3. Approximately replicating the shape of the fundus 3 is sufficient in order to simplify positioning the cryoballoon 6 within the stomach 1.

Figure 8:
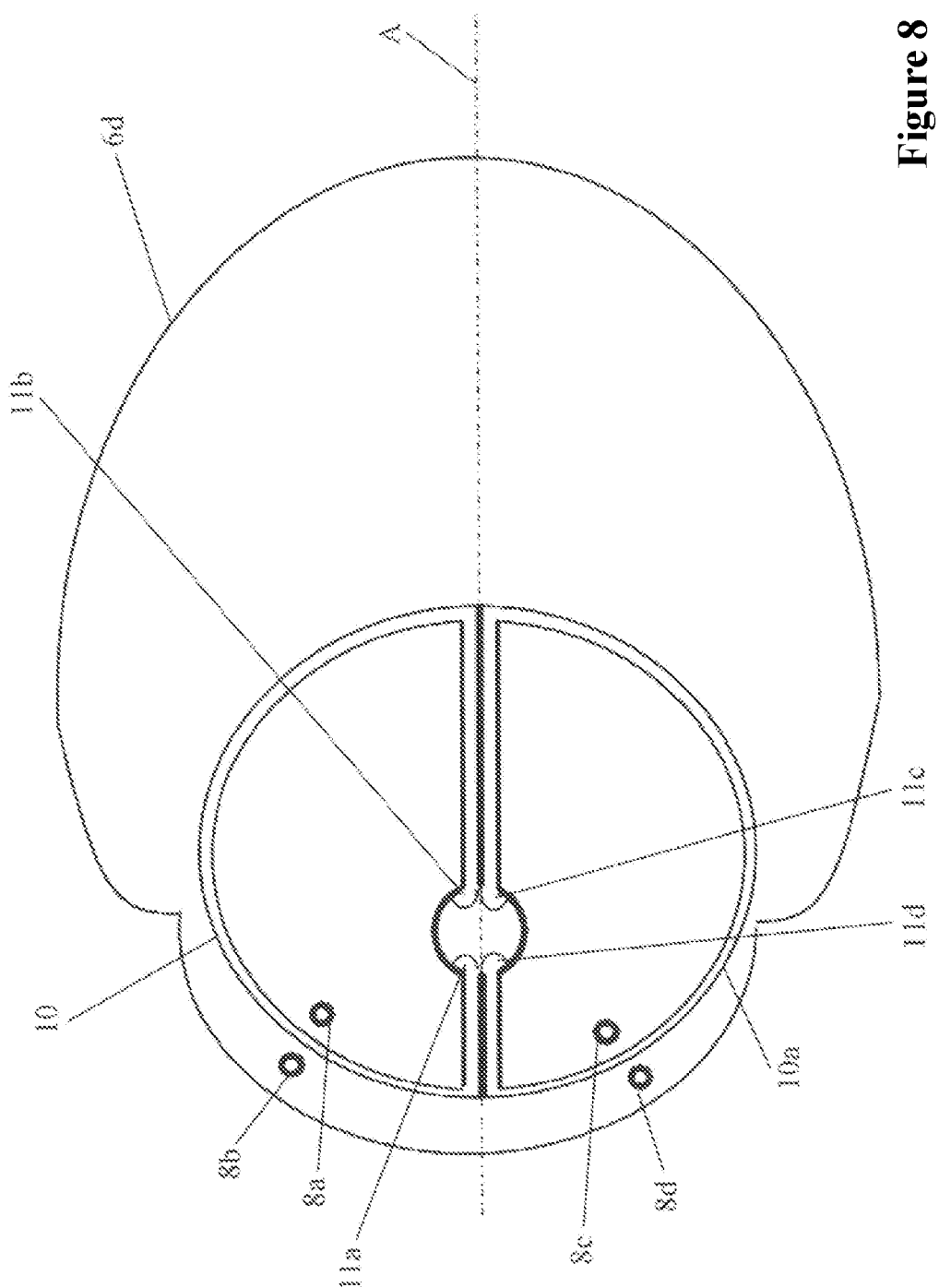
FIG. 8 is a schematic view of a fourth embodiment of a cryoballoon.

FIG. 8 shows a schematic view of a fourth embodiment of the cryoballoon, in the form of the cryoballoon 6d. The shape of the cross-sectional area of the cryoballoon 6d is reniform, but mirror-symmetrical with respect to the axis A in FIG. 8.

The first cooling arrangement 10 lies on one side of the plane of symmetry A, completely within one half of the cryoballoon 6d. The cryoballoon 6d also comprises a second cooling arrangement 10a in the form of a cooling conduit which in the present example likewise consists of a cooling conduit connected to conveying conduits 11c and 11d through which a cooling medium can be fed to the cooling conduit 10a and drained from the cooling conduit 10a again. The second cooling conduit 10a is situated completely on the other side of the cryoballoon 6d with respect to the plane of symmetry A. It should be noted that a second cooling arrangement 10a such as is shown in FIG. 8 can be combined with any other embodiments of the cryoballoon 6. If there are multiple cooling arrangements, different types of cooling arrangements can be combined with each other. One cooling arrangement can then for example be a cooling conduit, and one cooling arrangement can be one or more Peltier elements.

The measuring electrodes 8a and 8b are arranged on both sides of the first cooling arrangement 10. The two measuring electrodes 8c and 8d are also arranged on both sides of the second cooling arrangement 10a. All the measuring electrodes 8a to 8d are connected to the evaluation electronics 9 in order to measure the impedance of the tissue between the pair of measuring electrodes 8a and 8b and the pair of measuring electrodes 8c and 8d, respectively. Depending on the progress of ablation in the two regions, the operation of the corresponding cooling arrangement can be controlled independently of the operation of the other cooling arrangement.

In a modification of this embodiment, the two cooling conduits 10 and 10a can also be connected to each other and thus form a complete ring along the entire length of the contact curve 7. In this case, at least two of the conveying conduits are optional. Likewise, only two of the measuring electrodes 8 are required, i.e. this embodiment has at least two measuring electrodes and a cooling arrangement which extends along the entire length of the contact curve 7, wherein it can also be a single cooling arrangement. This enables circumferential ablation, the progress of which can be tracked via the measuring electrodes 8 and the evaluation electronics 9.

When using a catheter system in accordance with the invention, the distal end of the catheter 5 is inserted, together with the deflated cryoballoon 6, into the fundus 3 of the stomach 1. The cryoballoon 6 is then inflated, for example by filling it with a filling medium through a filling conduit which extends on or in the catheter 5. The catheter 5 is then retracted, together with the inflated cryoballoon 6, in the proximal direction until the cryoballoon 6 abuts the wall of the stomach 1 along the contact curve 7, wherein the cryoballoon 6 is aligned, for example by observing the markers 12 by means of X-ray radiation, such that the first cooling arrangement abuts the region of the wall of the stomach 1 which is to be cooled. The region to be cooled is either an anterior region of the stomach, for ablating the anterior vagal trunk, or a region on the posterior gastric wall, for ablating the posterior vagal trunk.

The progress of ablation can be controlled by an impedance measurement by means of the measuring electrodes 8 and the evaluation electronics 9. If the measured impedance exceeds a predetermined limit value, then ablation is assumed to be complete.

Once one trunk of the vagus nerve has being ablated, the cryoballoon 6 can be realigned, for example around the longitudinal axis of the catheter 5, such that the other trunk of the vagus nerve can be ablated.

Multiple ablations can be performed in sequence by advancing and retracting the cryoballoon 6. The fill level of the cryoballoon is optionally altered between two ablations, in order to adapt the contact curve 7.

Once ablation is complete, the cryoballoon 6 is deflated, for example by siphoning or bleeding the filling medium inside of the cryoballoon 6. The catheter 5 can then be removed, together with the cryoballoon 6, from the stomach 1.

In an alternative application, ablation is performed not just on a part of the vagus nerve 4, but rather circumferential ablation is performed along the entire contact curve 7. The sequence for this is similar to that of partial ablation; aligning the cryoballoon around the axis of the catheter 5 is however optional, particularly if the cryoballoon is a rotationally symmetrical cryoballoon 6. Within the framework of the disclosure, the measuring electrodes 8*a* and 8*b* and the evaluation electronics 9 are however not optional in the case of circumferential ablation.

The invention claimed is:

1. A catheter system for cryoablation of a stomach, comprising:
    a catheter and at least one inflatable cryoballoon which is fastened to the catheter that exhibits a contact curve along which the at least one inflatable cryoballoon can be brought into contact with a fundus,
    wherein the contact curve is a closed curve on a surface of the at least one inflatable cryoballoon, and the at least one inflatable cryoballoon contains a first cooling arrangement which extends along less than three quarters of a length of the contact curve, and
    wherein a proximal end of the at least one inflatable cryoballoon comprises a region in which the contact curve extends and a cross-sectional area of the at least one inflatable cryoballoon increases continuously from the proximal end to a distal end.

2. The catheter system according to claim 1, wherein the at least one inflatable cryoballoon comprises two measuring electrodes which are arranged on its surface on different sides of the contact curve.

3. The catheter system according to claim 2, further comprising evaluation electronics configured to measure the impedance between the two measuring electrodes.

4. The catheter system according to claim 1, wherein the at least one inflatable cryoballoon exhibits a shape of at least a part of the fundus.

5. The catheter system according to claim 1, wherein the first cooling arrangement extends over at most half the length of the contact curve.

6. The catheter system according to claim 1, wherein the first cooling arrangement comprises at least one Peltier element.

7. The catheter system according to claim 1, wherein the first cooling arrangement is a cooling conduit for a cooling medium, and the catheter contains at least one conveying conduit connected to the cooling conduit, for the cooling medium.

8. The catheter system according to claim 1, wherein the at least one inflatable cryoballoon contains a second cooling arrangement that extends along the contact curve in a region which is not occupied by the first cooling arrangement.

9. The catheter system according to claim 1, wherein the at least one inflatable cryoballoon comprises at least one radiopaque marker.

* * * * *